(12) United States Patent
Simon-Lopez

(10) Patent No.: US 7,586,589 B2
(45) Date of Patent: **\*Sep. 8, 2009**

(54) METHODS OF DETERMINATION OF RESPONSIVENESS TO ERYTHROPOIETIN TREATMENT

(75) Inventor: Ramon Simon-Lopez, St. Cergue (CH)

(73) Assignee: Beckman Coulter, Inc., Fullerton, CA (US)

( * ) Notice: Subject to any disclaimer, the term of this patent is extended or adjusted under 35 U.S.C. 154(b) by 245 days.

This patent is subject to a terminal disclaimer.

(21) Appl. No.: 11/524,635

(22) Filed: Sep. 21, 2006

(65) Prior Publication Data

US 2007/0072170 A1    Mar. 29, 2007

Related U.S. Application Data

(60) Provisional application No. 60/719,848, filed on Sep. 24, 2005.

(51) Int. Cl.
*G01N 33/49* (2006.01)
*G01N 33/48* (2006.01)

(52) U.S. Cl. .......................................... 356/39; 356/40
(58) Field of Classification Search .................. None
See application file for complete search history.

(56) References Cited

U.S. PATENT DOCUMENTS

| 2,656,508 | A | 10/1953 | Coulter |
| 3,810,011 | A | 5/1974 | Coulter et al. |
| 4,521,518 | A | 6/1985 | Carter et al. |
| 4,528,274 | A | 7/1985 | Carter et al. |
| 5,125,737 | A | 6/1992 | Rodriguez et al. |
| 5,763,280 | A | 6/1998 | Li et al. |
| 5,834,315 | A | 11/1998 | Riesgo et al. |
| 5,882,934 | A | 3/1999 | Li et al. |
| 5,935,857 | A | 8/1999 | Riesgo et al. |
| 6,573,102 | B2 | 6/2003 | Li et al. |
| 6,706,526 | B2 | 3/2004 | Lang et al. |

OTHER PUBLICATIONS

Lima et al. Comparison of Red Blood Cell Distribution Width and a Red Cell Discriminant Function Incorporating Volume Dispersion for Distinguishing Iron Deficiency From Beta Thalassemia Trait in Patients With Microcytosis; Sao Paulo Medical Journal, vol. 114, No. 5 (1996) pp. 1265-1269.*
Kotisaari et al. The Advia 120 Red Blood Cell and Reticulocyte Indices are Useful in Diagnosis of Iron-Deficiency Anemia; European Journal of Haematology, vol. 68 (2002) pp. 150-156.*
Goodnough, et al, "Erythropoietin, iron, and erythropoiesis", Blood, Aug. 1, 2000, vol. 96, No. 3, pp. 823-833.
Cooper, et al, "Reticulocyte changes after experimental anemia and erythropoietin treatment of horses", J. Appl. Physiol. 1st week of Sep. 2005, vol. 99, pp. 915-921.
Home Page of Journal of Applied Physiology, May 15, 2007. Internet <URL: http://jap.physiology.org>. Indicates publication of a new edition of journal within the first week of the month of publication.
Weiss, G., et al, "Effect of iron treatment on circulating cytokine levels in ESRD patients receiving recombinant human erythropoietin", Kidney Int'l, vol. 64 (2003), pp. 572-578.
Suominen, P., "Serum Transferrin Receptor and Transferrin Receptor-Ferritin Index Identify Healthy Subjects with Subclinical Iron Deficits", Blood, vol. 92, No. 8 1998; pp. 2934-2939.
Eknoyan, G., et al, "Continuous Quality Improvement: DOQI Becomes K/DOQI and is Updated", Am J of Kidney Diseases, vol. 37, No. 1 (2001; pp. 179-194.
Weiss, G., et al, Review Article, Medical Progress: "Anemia of Chronic Disease", N Engl J Med 352:10 (2005); pp. 1011-1023.
Callum G. Fraser, "The Application of Theoretical Goals Based on Biological Variation Data in Proficiency Testing", Arch Pathol Lab Med, vol. 112, Apr. 1988; pp. 404-415.

* cited by examiner

*Primary Examiner*—Jon P Weber
*Assistant Examiner*—Paul C. Martin
(74) *Attorney, Agent, or Firm*—Cuspa Technology Law Associates; Mitchell E. Alter

(57) ABSTRACT

Methods for determining the responsiveness of a patient to recombinant human erythropoietin therapy are disclosed. In one approach, the method includes obtaining a volume-Hgb factor (VHf) defined as a product function of MCV and Hgb from a patient's blood sample; comparing VHf to a predetermined criterion; and reporting indication of responder if VHf meets the predetermined criterion. The method further includes using a RBC size-hemoglobin factor (RSHf) defined as a product function of MCV, MRV and Hgb, or using a function of VHf and RDW for determining the responsiveness. In another approach, the method includes using a RBC size factor (RSf) defined as a product function of MCV and MRV, in combination with transferrin saturation (TSAT) for determining the responsiveness to the erythropoietin therapy.

13 Claims, 4 Drawing Sheets

METHODS OF DETERMINATION OF RESPONSIVENESS TO ERYTHROPOIETIN TREATMENT

CROSS REFERENCE TO RELATED APPLICATION

This application claims the benefit under 35 USC 119 (e) of the provisional patent application Ser. No. 60/719,848, filed on Sep. 24, 2005, which is herein incorporated by reference in its entirety.

FIELD OF THE INVENTION

The present invention relates to methods for determining the responsiveness of a patient to erythropoietin/intravenous iron therapy using specific functions of red blood cell and reticulocyte parameters.

BACKGROUND OF THE INVENTION

Recombinant human erythropoietin (r-HuEPO) is a relatively new treatment, useful in treating the anemia in renal failure patients in treatment with hemodialysis, however, it is necessary to supply iron and other nutrients to the patients because the requirements to iron and other nutrients increase when r-HuEPO is administered. Typically, in addition to r-HuEPO, a certain dose of intravenous iron is given, depending on the patient's iron status, to provide required iron supply. However, on the other hand, the toxicity of excess iron can pose life threatening risks to the patients. Careful evaluation of the iron status is of pivotal importance in end-stage renal disease patients before and during r-HuEPO therapy, which helps to determine appropriate treatment protocol.

In healthy individuals, iron concentrations in various tissues remain in a state of precise balance. Daily intake and loss of iron are small and body iron is reutilized. In patients with end-stage renal disease (ESRD), however, the supply of iron to the bone marrow may not be adequate to sustain normal erythropoiesis. Iron deficiency may also be caused by an increase in iron demand. Severe anemia associated with ESRD is mainly due to a deficiency in erythropoietin, a hormone produced by healthy kidneys. Replacement therapy with recombinant human erythropoietin, a stimulant of RBC formation, can correct this type of anemia in dialysis patients. However, r-HuEPO therapy increases the demand for iron. When iron stores cannot be mobilized quickly enough to be transported to the bone marrow where iron is needed for the production of new RBCs, a functional iron deficiency (FID) may result, despite an adequate iron supply. This functional iron deficiency can delay or diminish the response to r-HuEPO therapy. Iron supplementation is required to restore and maintain proper iron balance and to ensure optimal therapeutic response to r-HuEPO therapy.

Most recently, it has been reported that r-HuEPO is also a cytokine, which helps to cure the functional iron deficiency. Weiss et al. have shown that maintaining the serum ferritin of the ESRD patients higher than 150 ng/ml and only administering r-HuEPO without iron had no significant differences from the group of patients that received r-HuEPO/iron treatment during the follow up of three months. This has been attributed to the effect that r-HuEPO helps to liberate the iron that is blocked in the iron storage due to the inflammatory process (Weiss G, et al. Effect of iron treatment on circulating cytokine levels in ESRD patients receiving recombinant human erythropoietin. *Kidney Int* 2003; 64:572-8).

The most commonly used iron status parameters at present are transferrin saturation (TSAT) and serum ferritin (SF). However, both are indirect measures of iron status. Transferrin is a transport protein that contains two iron binding sites by which it transports iron from storage sites to erythroid precursors. TSAT (i.e., the percentage of total binding sites that are occupied by iron) is a measure of iron that is available for erythropoiesis. TSAT is calculated by dividing the serum iron by the total iron binding capacity (TIBC), a measurement of circulating transferrin, and multiplying by 100. Ferritin is a storage protein that is contained primarily within the reticuloendothelial system (RES), with some amounts released in the serum. Under conditions of iron excess, ferritin production increases to offset the increase in plasma iron. The level of ferritin in the serum, therefore, reflects the amount of iron in storage.

In normal individuals, SF levels range from 22 to 220 ng/ml and TSAT levels range from 20% to 40% (Suominen, P, et al., Serum Transferrin Receptor and Transferrin Receptor-Ferritin Index Identify Healthy Subjects With Subclinical Iron Deficits, *Blood*, Vol. 92, No. 8, 1998: pp 2934-2939). In patients without renal impairment, SF levels <22 ng/ml and TSAT <16% are indicative of depleted iron stores and absolute iron deficiency. In patients with chronic kidney disease, absolute iron deficiency is characterized by SF levels <100 ng/ml and TSAT <20%. Functional iron deficiency may be more difficult to diagnose since iron status parameters may indicate adequate iron stores. There are different criteria in defining FID, one of them is published by the Kidney Disease Outcomes Quality Initiative-K/DOQI (Eknoyan G, et al. Continuous quality improvement: DOQI becomes K/DOQI and is updated. National Kidney Foundation's Dialysis Outcomes Quality Initiative. *Am J Kidney Dis.*, 2001 January;37 (1):179-194), as shown in the following table.

| Definition of Functional Iron Deficiency (FID) and Absolute Iron Deficiency (AID) by Kidney Disease Outcomes, Quality Initiative K/DOQI (U.S.A) | | |
|---|---|---|
| | Ferritin µg/l | |
| | <100 | 100-800 |
| TSAT <20% | AID | |
| TSAT 20%-50% | | FID |

Because patients on r-HuEPO therapy may have adequate iron stores (as reflected by SF ≧100 ng/ml) but still have functional iron deficiency, the use of alternative iron parameters, for example, serum transferrin receptors (sTfR), alone or in combination with serum ferritin has been suggested in these patients (Weiss, G. et al. Review Article, Medical progress: Anemia of Chronic Disease. *N Engl J Med* 2005; 352:1011-23).

The reliability of using the serum ferritin to assess the iron status has been criticized, because serum ferritin is also a reactant phase protein, it is often elevated in the course of disease. Transferrin saturation has also been criticized, because the unreliability of serum iron measurements. Furthermore, transferrin saturation is affected by certain diseases, such as liver insufficiency, malnutrition, proteinuria, exudative enteropathy and acute phase reaction. In the past few years, numerous articles have reported that only using biochemical parameters to assess iron status is not sufficient for managing the r-HuEPO therapy.

Recently, the use of reticulocyte and red blood cell parameters has been suggested for detection of iron deficiency and for assistance in managing the r-HuEPO therapy. These new parameters include reticulocyte hemoglobin content (CHr) and percentage hypochromic red blood cells. More recently, RBC-Y (the mean value of the forward light scatter histogram within the mature erythrocyte population) and RET-Y (the mean value of the forward light scatter histogram within the reticulocyte population), which are obtained in the reticulocyte measurement on the SYSMEX® XE-2100 automated hematology analyzer have also been suggested.

Transferrin receptors on the cell surface of RBC precursors bind iron-bound transferrin, allowing the transport of iron from the plasma into the cells. Under conditions of iron deficiency, there is an upregulation of these receptors to allow more efficient uptake of transferrin. The concentration of transferrin receptors on the cell surface correlates with transferrin uptake. In hemodialysis patients who are not treated with r-HuEPO therapy, sTfR levels are higher among those who are iron deficient than among those who are iron replete. However, in several studies, hemodialysis patients treated with r-HuEPO therapy had similar sTfR levels regardless of iron status. Therefore, sTfR may not be an accurate marker of iron status in hemodialysis patients.

Reticulocytes are immature red blood cells (RBCs) with a life span of only 1 to 2 days. When these are first released from the bone marrow, measurement of their hemoglobin content can provide the amount of iron immediately available for erythropoiesis. A less than normal hemoglobin content in these reticulocytes is an indication of inadequate iron supply relative to demand. The amount of hemoglobin in these reticulocytes also corresponds to the amount of hemoglobin in mature RBCs. CHr is defined by the formula (CHr=MCVr×CHCMr), wherein MCVr is the mean reticulocyte cell volume and CHCMr is the mean hemoglobin concentration of reticulocytes which is obtained by an optical cell-by-cell hemoglobin measurement on the Bayer ADVIA 120 hematology analyzer. CHr has been evaluated in several studies as a test for functional iron deficiency and has been found to be highly sensitive and specific. However, exact threshold-values have not been established. Threshold values vary depending on the laboratory and instrument used.

Epoetin is effective in stimulating production of red blood cells, but without an adequate iron supply to bind to heme, the red blood cells will be hypochromic, i.e., low in hemoglobin content. Thus, in states of iron deficiency, a significant percentage of red blood cells leaving the bone marrow will have a low hemoglobin content. By measuring the percentage of red blood cells with hemoglobin content <28 g/dl, iron deficiency can be detected. Hypochromic red cells percentages >10% have been correlated with iron deficiency. Hypochromic red cell percentage (referred to as % Hypo) is reported by Bayer ADVIA® 120 hematology analyzer based on the optical cell-by-cell hemoglobin measurement.

Additionally, the red-cell distribution width (RDW) has been used in combination with other parameters for the classification of anemias. It reflects the variation in the size of the red cells and can be used to detect subtle degrees of anisocytosis. RDW is computed directly form the RBC histogram. Two different calculated values have been provided on hematology analyzers. The RDW-CV is measured as a ratio of the width of the distribution curve at one standard deviation divided by the MCV. The RDW-SD is a direct measurement of the distribution width at the 20% frequency level. Normally, the size distribution curve for red blood cells is quite symmetrical, with an RDW-CV value of 10±1.5% and an RDW-SD of 42±5 (fl). A high RDW, which means a greater variation in cell size, is caused by either the appearance of macrocytic or microcytic cells. An elevated red-cell distribution width appears to be the earliest hematological manifestation of iron deficiency.

As can be appreciated from the above, determining iron status, more particularly FID, is important for determining appropriate a treatment protocol. However, it is even more important and desirable, from a practical standpoint, if the doctors can effectively and reliably predict the patient's responsiveness to the r-HuEPO/intravenous iron treatment based on those available clinical chemistry and hematology parameters, as this can avoid unnecessary and expensive r-HuEPO therapy, and reduce the life threatening risks associated with inappropriate r-HuEPO/intravenous iron treatment given to the non-responders.

SUMMARY OF INVENTION

In one aspect, the present invention provides methods of using several functions of red blood cell and reticulocyte parameters provided on hematology analyzers for determining responsiveness of a patient to recombinant human erythropoietin therapy.

In one embodiment, the method comprises analyzing a first blood sample of the patient on a hematology analyzer and obtaining a mean cell volume of red blood cells (MCV) and a mean cell volume of reticulocytes (MRV) of the first blood sample; obtaining a RBC size factor (RSf) defined as a product function of MCV and MRV; analyzing a second blood sample of the patient on a clinical chemistry analyzer and obtaining transferrin saturation (TSAT) of the second blood sample; comparing the TSAT and RSf to predetermined criteria; and reporting an indication of a responder if the TSAT and the RSf meet the predetermined criteria. Herein, RSf can be either $RSf_1$ defined by the formula of $(MCV \times MRV)^{1/2}$, or $RSf_2$ defined by the formula of $(MCV \times MRV)/100$.

In a further embodiment, the method comprises analyzing a blood sample of the patient on a hematology analyzer and obtaining MCV and a total hemoglobin concentration (Hgb) of the blood sample; obtaining a volume-hemoglobin factor (VHf) defined as a product function of the MCV and the Hgb; comparing the VHf to a predetermined VHf criterion; and reporting an indication of a responder if the VHf meets the predetermined VHf criterion. In a preferred embodiment, VHf is defined by the formula of $(MCV \times Hgb)/100$.

Moreover, the method can further comprise obtaining red blood cell distribution width (RDW) from the analysis; obtaining a volume-hemoglobin/distribution factor (VHDWf) defined as a function of MCV, Hgb and RDW; comparing the VHDWf to a predetermined VHDWf criterion; and reporting an indication of the responder if the VHDWf meets the predetermined VHDWf criterion. In one embodiment, VHDWf is defined by the formula of $(MCV \times Hgb)/(RDW \times 10)$.

Additionally, the method can further comprise analyzing a second blood sample of the patient on a clinical chemistry analyzer, obtaining transferrin saturation (TSAT), and using TSAT in combination with VHf in determining responsiveness of the patient.

In another embodiment, the method can comprise. obtaining a RBC size-hemoglobin factor (RSHf) defined as a product function of MCV, MRV and Hgb; comparing the RSHf to a predetermined RSHf criterion; and reporting an indication of the responder if the RSHf meets the predetermined RSHf criterion. In one embodiment, RSHf is defined as (MCV×

MRV×Hgb)/1000. The method can further include using TSAT in combination with RSHf in determining responsiveness of the patient.

In yet a further embodiment, the method comprises using Hgb for determining responsiveness of a patient to recombinant human erythropoietin therapy, if the patent's TSAT is between 20% and 30%.

In a further aspect, the method of the present invention further includes using these functions to assisting in determining the treatment protocols.

The advantages of the present invention will become apparent from the following description taken in conjunction with the accompanying drawings showing exemplary embodiments of the invention.

DETAILED DESCRIPTION OF THE INVENTION

Figure 1A:
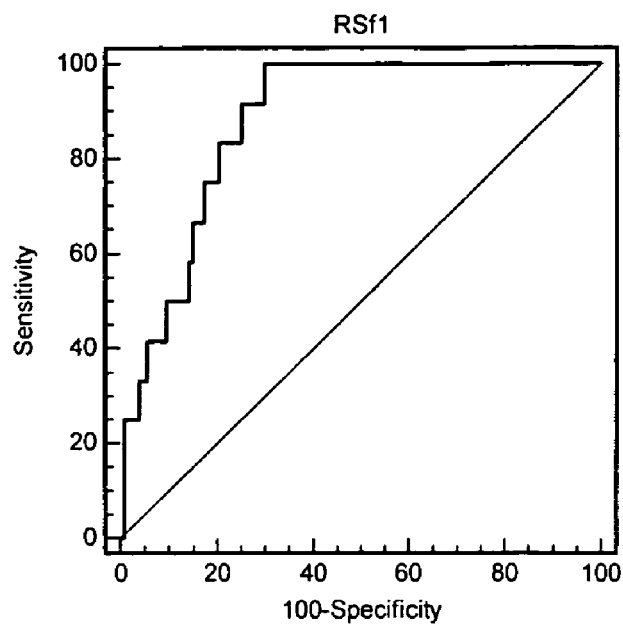
FIGS. 1A and 1B are the ROC curves of $RSf_1$, and $RSf_2$, respectively, for patients having TSAT <20%.

In one aspect, the present invention provides methods of determining the responsiveness of a patient to r-HuEPO therapy. As typically a patient is also given iron intravenously, the therapy is herein also referred to as r-HuEPO/intravenous iron (r-HuEPO/i.v. iron) treatment.

In one embodiment, the method of determining the responsiveness of a patient to r-HuEPO/i.v. iron treatment uses a product function of the mean cell volume of red blood cells (MCV) and the mean cell volume of reticulocytes (MRV) of a blood sample, which is herein referred to as RBC size factor (RSf). More specifically, the method comprises the following steps: (a) analyzing a first blood sample of the patient on a hematology analyzer and obtaining MCV and MRV of the first blood sample; (b) obtaining RSf from the first blood sample; (c) analyzing a second blood sample of the patient on a clinical chemistry analyzer and obtaining transferrin saturation (TSAT) from the second blood sample; (d) comparing the obtained TSAT and RSf to the predetermined criteria; and (e) reporting an indication of a responder if the obtained TSAT and RSf meet the predetermined criteria.

Herein, the responder is defined as a patient who achieves 10% or more increase in total hemoglobin concentration (Hgb) in the next blood analysis during the r-HuEPO/i.v. iron treatment, which is typically one month from the immediate preceding blood analysis. The non-responder is defined as a patient who does not achieve this level of an increase in Hgb in the next blood analysis.

In one preferred embodiment, RSf is defined by the formula of $(MCV \times MRV)^{1/2}$, which is herein referred to as $RSf_1$. In one exemplary embodiment, the predetermined $RSf_1$ criteria for defining the responder are TSAT less than 20% and $RSf_1$ less than 105.1, as described more fully hereinafter. In an alternative embodiment, RSf is defined by the formula of $(MCV \times MRV)/100$, which is herein referred to as $RSf_2$. In an exemplary embodiment, the predetermined $RSf_2$ criteria for defining the responder are TSAT less than 20% and $RSf_2$ less than 110.5, as described more fully hereinafter.

It can be appreciated that when MCV is measured, what is measured is the average size or volume of the red blood cells produced in a period of 120 days before the blood sample is drawn (with the exception when the mean life time of the red blood cells is reduced). On the other hand, when MRV is measured, what is measured is the size or volume of the more recently produced red blood cells, within a period of less than 3 days before the blood sample is drawn. Since in both mature red blood cells and the reticulocytes above 90% cellular contents are hemoglobin, the sizes of these blood cells directly correlate to the hemoglobin contents of the cells. RSf, as a product function of both MCV and MRV, hence, reflects indirectly the cellular hemoglobin contents of both the reticulocytes and the mature red blood cells.

Typically, on a hematology analyzer several aliquots of a blood sample are analyzed concurrently to obtain different hematology parameters such as red blood cell and reticulocyte parameters, and hemoglobin concentration, as described more fully hereinafter. The blood sample is collected in a test tube containing an anticoagulant, such as EDTA or heparin. Typically, the blood samples used for hematology analysis and clinical chemistry analysis are collected into different test tubes, as the preservatives can be different. The existing method for measurement of TSAT known in the art can be used for the purpose of the present invention.

For measuring the red blood cells, a blood sample is typically diluted substantially with a diluent in a sample chamber or bath. Using an impedance measurement with a non-focused flow aperture, the blood sample can be diluted with a dilution ratio of about 6250:1. When a focused-flow flow cell is used for the measurement, the dilution ratio can be substantially lower, such as 290:1. To maintain red blood cell volume and morphology during their measurements on a hematology analyzer, an isotonic diluent is used for diluting the blood sample. Typically, the diluent contains one or more alkaline metal salts. Various commercially available isotonic blood diluents can be used for diluting the blood sample. Suitable examples include, but are not limited to, the diluents described in U.S. Pat. Nos. 4,521,518, 4,528,274, 5,935,857 and 6,706,526.

When a particle or a blood cell, suspended in a conductive solution, passes through a flow cell or an aperture, an electrical signal, or a pulse, can be measured due to the increase of impedance. The electrical pulses have been used for counting the number of blood cells of a blood sample. On the other hand, the pulse shape, height and width are directly related to the volume or size of a particle, and can be converted to the volume of the cell measured. The detection methods and apparatus used for blood cell counting and sizing by a blood analyzer equipped with a DC impedance measurement device are generally described in U.S. Pat. Nos. 2,656,508, 3,810,011 and 5,125,737, which are herein incorporated by reference in their entirety. Herein, the phrase "blood cell sizing" refers to the cell volume measurement.

Alternatively, low angle light scatter measurement can also be used for counting and sizing the blood cells. Herein, the term "low angle light scatter" refers to light scatter signals measured in a range in less than 10° from the incident light.

In the cell volume measurement, a cell volume distribution histogram is obtained. For the red blood cell measurement, the obtained histogram is referred to as a red blood cell distribution histogram. For a normal blood sample, a narrow and well defined red blood cell distribution, typically a Gaussian distribution, is obtained. For clinically abnormal blood samples, various distortions of the distribution have been observed, such as a shift of the distribution to either higher or lower volume side, asymmetric distribution, population extension on either the higher or lower volume side, or both sides. The mean cell volume (MCV) and red blood cell distribution width (RDW) are calculated from the red blood cell distribution histogram.

The total hemoglobin concentration (Hgb) of a blood sample is typically measured on an automated hematology analyzer by mixing an aliquot of the blood sample with a lytic reagent. Upon exposing to the lytic reagent, the red blood cells are completely lysed, and hemoglobins are released into the sample mixture, which upon contacting with a ligand in the lytic reagent forms a chromogen. The hemoglobin chromogen is then measured by UV-VIS spectroscopy at a predetermined wavelength, and Hgb is calculated from the measurement.

One lysing reagent system suitable for measuring Hgb comprises an isotonic blood diluent, such as the diluents described in U.S. Pat. Nos. 4,521,518, 4,528,274, 5,935,857 and 6,706,526, and a lysing reagent, such as the lysing reagents described in U.S. Pat. Nos. 5,763,280, 5,834,315 and 6,573,102, these are hereby incorporated by reference in their entirety. Alternatively, the reagent system can also be a single lysing reagent as described in U.S. Pat. No. 5,882,934 which is hereby incorporated by reference in its entirety. Furthermore, various lytic reagents known in the art for measurement of hemoglobin can be used for the purpose of the present invention.

Reticulocytes in a blood sample are measured and reported on several high end hematology analyzers in routine sample analysis, using light scatter, absorption, impedance and/or combinations thereof. Most commonly reported parameters include reticulocyte percent (RET %) and absolute number (RET#), mean reticulocyte volume (MRV), and immature reticulocyte fraction (IRF). Depending on the specific measurement method, other reticulocyte parameters are also provided by the hematology analyzers.

On the Coulter GEN*S™ hematology analyzer (Beckman Coulter, Inc. Fullerton, Calif.), several aliquots of a blood sample are analyzed concurrently in different analysis modes. In the CBC mode, a first aliquot of a blood sample is diluted by a blood diluent to form a first sample mixture, and red blood cells and platelets are measured from the first sample mixture. At the same time, a second aliquot of the blood sample is mixed with a blood diluent and a lytic reagent to form a second sample mixture, and hemoglobin and white blood cells are measured from the second sample mixture. Various red blood cell parameters, among others, are reported from these measurements, which include mean cell volume (MCV), red blood cell distribution width (RDW), total hemoglobin concentration (Hgb), and derivative parameters, such as mean corpuscular hemoglobin (MCH), mean corpuscular hemoglobin concentration (MCHC), and etc. The RDW reported on this hematology analyzer is RDW-CV, which is measured as a ratio of the width of the distribution curve at one standard deviation divided by the MCV.

In the Retic mode, a third aliquot of the blood sample is mixed with a reticulocyte stain reagent which contains methylene blue, and then mixed with a lysing/fixing reagent to form the third sample mixture. Methylene blue, a non-fluorochrome dye, is used to precipitate the residual RNA within the reticulocytes, thereby achieving differentiation of the reticulocytes from mature red blood cells. The third sample mixture is then measured by the VCS detection method. Among other reticulocyte parameters, MRV, mean spherized cell volume (MSCV), immature reticulocyte fraction (IRF), and high light scatter reticulocyte percent and absolute number (HLR % and #) are reported by the instrument.

Herein, the VCS detection method or technology refers to a multidimensional measurement of direct current (DC), radio frequency (RF), and medium angle light scatter (LS) signals generated by a cell passing through a focused flow cell. Among these three measurements, both DC and RF measurements are impedance measurements, which detect the increase of impedance as a cell carried in a conductive medium passes through the flow cell. This technology has been fully described in U.S. Pat. No. 5,125,737, which is herein incorporated by reference in its entirety.

The Example illustrates the utility of $RSf_1$ and $RSf_2$ in differentiating responders and non-responders to the r-HuEPO/i.v. iron treatment. As shown, 323 whole blood samples from 59 patients with renal failure in a treatment program of hemodialysis on alternate days were studied in a period of five months using various functions of red blood cell and reticulocyte parameters obtained on Coulter GEN*S hematology analyzer. Clinical chemistry parameters, TSAT and SF, were also obtained on clinical chemistry analyzers.

As shown in Table 3, from a t-student test, there is a statistically significant difference for both $RSf_1$ and $RSf_2$ between the responders and the non-responders. Receiver operating characteristic (ROC) analysis was performed for $RSf_1$ and $RSf_2$. It was found that for patients having TSAT <20%, the RBC size factor, both $RSf_1$ and $RSf_2$, were one of the most effective parameters in differentiating the responders and non-responders.

Figure 1B:
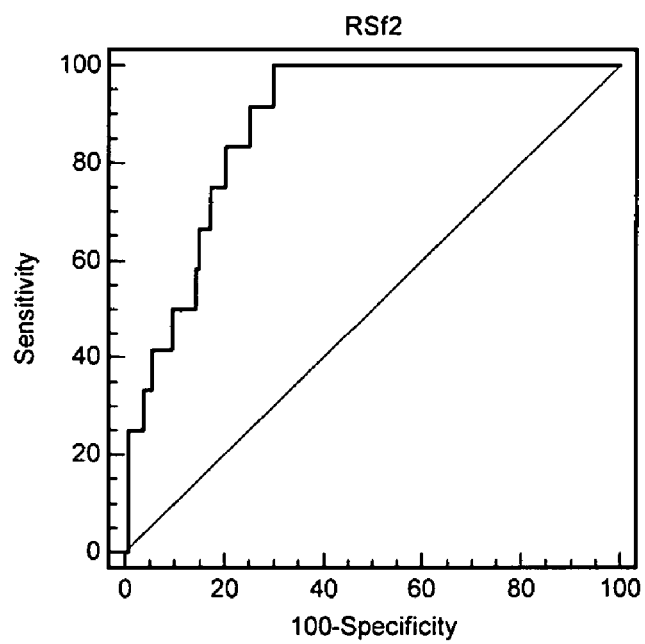

FIGS. 1A and 1B show the ROC curves of $RSf_1$ and $RSf_2$, respectively, for patients having TSAT <20%. On the y-axis is plotted sensitivity (true positive fraction) and on the x-axis is plotted 100-specificity (false positive fraction). A test with perfect discrimination has an ROC curve that passes through the upper left corner, where the true-positive fraction is 100% (perfect sensitivity). The theoretical curve for a test with no discrimination is 45° diagonal line from the lower left corner to the upper right corner. The closer the curve to the upper left corner, the higher the overall accuracy of the test is. Furthermore, the area under the ROC curve (AUC) is also a common measure of the clinical accuracy of a diagnostic test. The AUC from ROC analysis for $RSf_1$ was 0.898. With a cut-off $\leq 105.1$, $RSf_1$ had a sensitivity of 100% and a specificity of 72.3%, respectively. The AUC for $RSf_2$ was 0.898. With a cut-off $\leq 110.5$, $RSf_2$ also had a sensitivity of 100% and a specificity of 72%, respectively, for determining the responders and non-responders. Herein, the cut-off refers to the cut-off values of ROC analysis of $RSf_1$ and $RSf_2$, each as defined above, with MCV and MRV expressed in femtoliter (fl). These factors are used herein as indexes for determining the responsiveness to r-HuEPO therapy. From the results described above, both $RSf_1$ and $RSf_2$ had about the same ability in differentiating the responders and non-responders. These results indicate that both $RSf_1$ and $RSf_2$ are effective parameters in differentiating the responders and non-responders to the r-HuEPO therapy.

In a further embodiment, the method of the present invention of determining the responsiveness of a patient to r-HuEPO/i.v. iron treatment uses a product function of MCV and Hgb, which is herein referred to as volume-hemoglobin factor (VHf). More specifically, the method includes the following steps: (a) analyzing a blood sample of a patient on a hematology analyzer and obtaining MCV and Hgb of the blood sample; (b) obtaining VHf from the blood sample; (c) comparing the obtained VHf to the predetermined VHf criterion; and (d) reporting an indication of a responder if the VHf meets the predetermined VHf criterion.

Figure 2A:
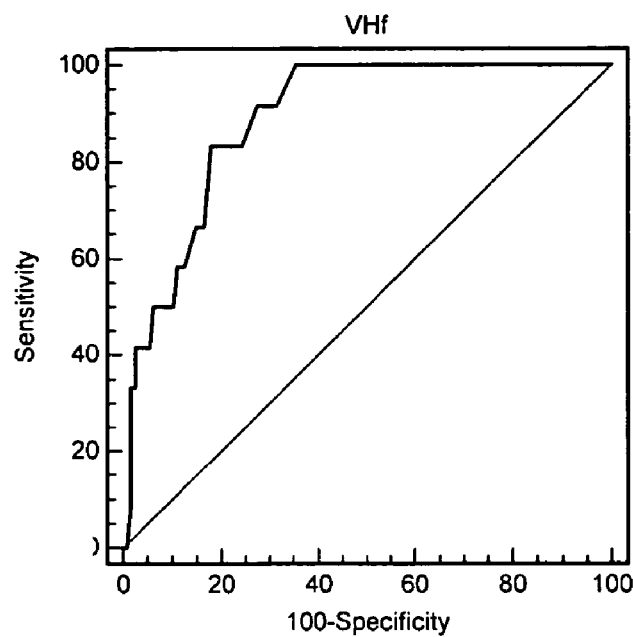
FIGS. 2A and 2B are the ROC curves of VHf for patients having TSAT <20%, and the patients having TSAT >20%, respectively.

In a preferred embodiment, VHf is defined by the formula of (MCV×Hgb)/100. As shown in Table 3, for patients having TSAT <20%, there is a statistically significant difference for VHf between the responders and the non-responders. FIG. 2A shows the ROC curve of VHf for patients having TSAT <20%. From the ROC analysis of VHf, the AUC was 0.889. With a cut-off $\leq 9.9$, VHf had a sensitivity of 91.7% and a specificity of 68.5%, respectively, for differentiating the responders and non-responders. Herein, the cut-off refers to the cut-off value of ROC analysis of VHf as defined by the formula of (MCV×Hgb)/100, with MCV expressed in femtoliter (fl) and Hgb expressed in gram per deciliter (g/dl). This factor is used herein as an index for determining the responsiveness to r-HuEPO therapy.

Figure 2B:
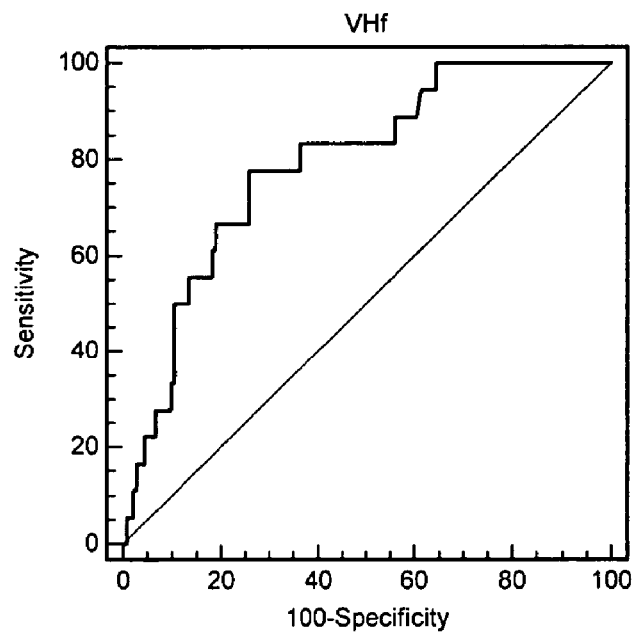

Furthermore, it has been found that VHf is also effective in differentiating the responders and non-responders for patients whose TSAT is higher than 20%. FIG. 2B shows the ROC curve of VHf for patients having TSAT >20%. The AUC from the ROA analysis of VHf for this group of patients was 0.789. With a cut-off $\leq 10.5$, VHf had a sensitivity of 77.8% and a specificity of 74.2%, respectively, for differentiating the responders and non-responders.

These results indicate that VHf may be used independently for determining the responders and the non-responders. Furthermore, as the cut-off values for VHf can be different for patients having TSAT <20%, and those having TSAT>20%, TSAT can be used in conjunction with VHf to more accurately determine the responders and non-responders.

In a further aspect of the present invention as described hereinafter, the instant method further includes using the parameters described above for determining the r-HuEPO/i.v. iron treatment protocol. For this purpose, the method of using VHf for determining the responsiveness of a patient to r-HuEPO/i.v. iron treatment can further include analyzing a further blood sample of the patient on a clinical chemistry analyzer, obtaining transferrin saturation (TSAT), and using TSAT in conjunction with VHf for determining a treatment protocol.

Moreover, it has also been found that a function of VHf and RDW (red blood cell distribution width) can be used for determining a patient's responsiveness to the r-HuEPO therapy. More specifically, the function is defined by the formula of (MCV×Hgb)/(RDW×10), which is referred herein as a volume-hemoglobin/distribution factor (VHDWf). Therefore, the method described above can further include obtaining (RDW) from the analysis in step (a); obtaining VHDWf; comparing VHDWf to a predetermined VHDWf criterion; and reporting an indication of a responder if VHDWf meets the predetermined VHDWf criterion.

Additionally, it is noted that in various other studies it has been found that VHf can also be used for detection of iron deficiency. Since microcytic anemia is a typical clinical condition resulted from iron deficiency, this factor has also been referred to as microcytic anemia factor (MAf).

In another embodiment, the method of the present invention of determining the responsiveness of a patient to the r-HuEPO/i.v. iron treatment uses a product function of MCV, MRV and Hgb, which is herein referred to as RBC size-hemoglobin factor (RSHf). More specifically, the method includes the following steps: (a) analyzing a first blood sample of the patient on a hematology analyzer and obtaining MCV, MRV and Hgb of the first blood sample; (b) obtaining RSHf of the first blood sample; (c) comparing the obtained RSHf to the predetermined criterion; and (d) reporting an indication of responder if the RSHf meet the predetermined criterion.

Figure 3A:
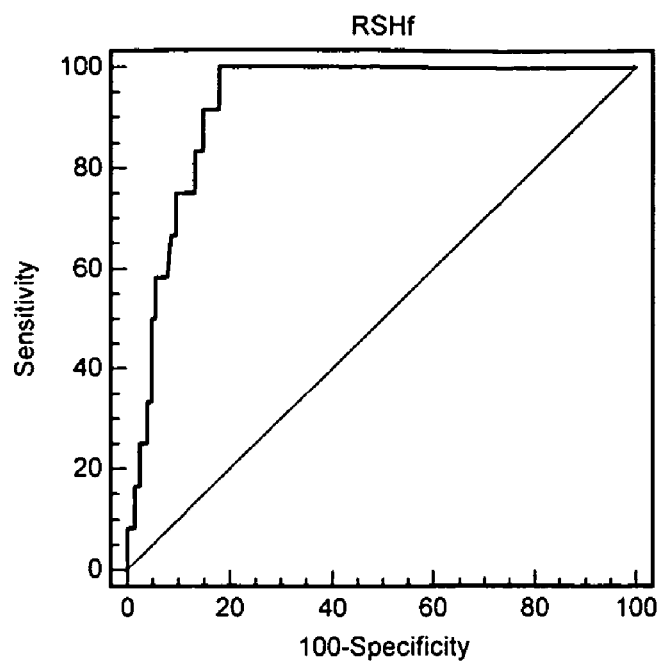
FIGS. 3A and 3B are the ROC curves of RSHf for patients having TSAT <20%, and the patients having TSAT >20%, respectively.
Figure 3B:
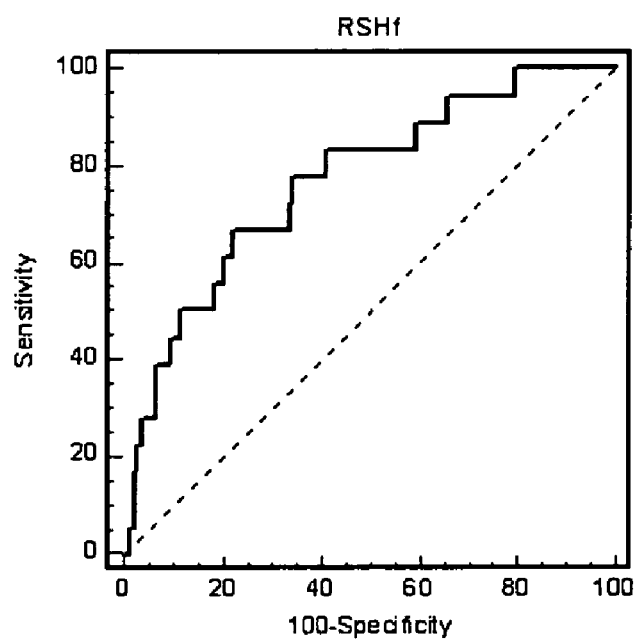

In a preferred embodiment, RSHf is defined by the formula of (MCV×MRV×Hgb)/1000. As shown in Table 3 and described in the Example, it has been found that RSHf is an effective parameter for differentiating the responders and non-responders to the r-HuEPO/i.v. iron treatment. FIGS. 3A and 3B show the ROC curves of RSHf for patients having TSAT <20%, and the patients having TSAT >20%, respectively. For the patients having TSAT <20%, the AUC from the ROC analysis for RSHf was 0.927. With a cut-off $\leq 111.5$, RSHf had a sensitivity of 100% and a specificity of 81.9%, respectively, for determining the responders and non-responders. For the patients having TSAT >20%, the AUC for RSHf was 0.766. With a cut-off >122.5, RSHf had a sensitivity of 66.7% and a specificity of 78.0%, respectively. Herein, the cut-off refers to the cut-off value of ROC analysis of RSHf, as defined by the formula of (MCV×MRV×Hgb)/1000, with MCV and MRV expressed in femtoliter (fl) and Hgb expressed in gram per deciliter (g/dl). This factor used herein as an index for determining the responsiveness to r-HuEPO therapy.

These results indicate that RSHf may be used independently for determining the responders and non-responders. Furthermore, as the cut-off value for RSHf can be different for patients having TSAT <20%, and those having TSAT>20%, TSAT can be used in conjunction with RSHf to more accurately determine the responders and non-responders. Moreover, TSAT level can also be used together with RSHf for determining treatment protocols of the r-HuEPO/i.v. iron treatment.

In yet a further embodiment, the present invention provides a method of determining the responsiveness of a patient to the r-HuEPO/i.v. iron treatment when the patient's TSAT is between 20% and 30%. More specifically, the method includes the following steps: (a) analyzing a first blood sample of the patient on a hematology analyzer and obtaining a total hemoglobin concentration (Hgb) of the first blood sample; (b) analyzing a second blood sample of the patient on a clinical chemistry analyzer and obtaining transferrin saturation (TSAT) of the second blood sample; (c) comparing obtained TSAT and Hgb to the predetermined criteria; and (e) reporting an indication of responder if the TSAT and the Hgb meet the predetermined criteria.

Figure 4:
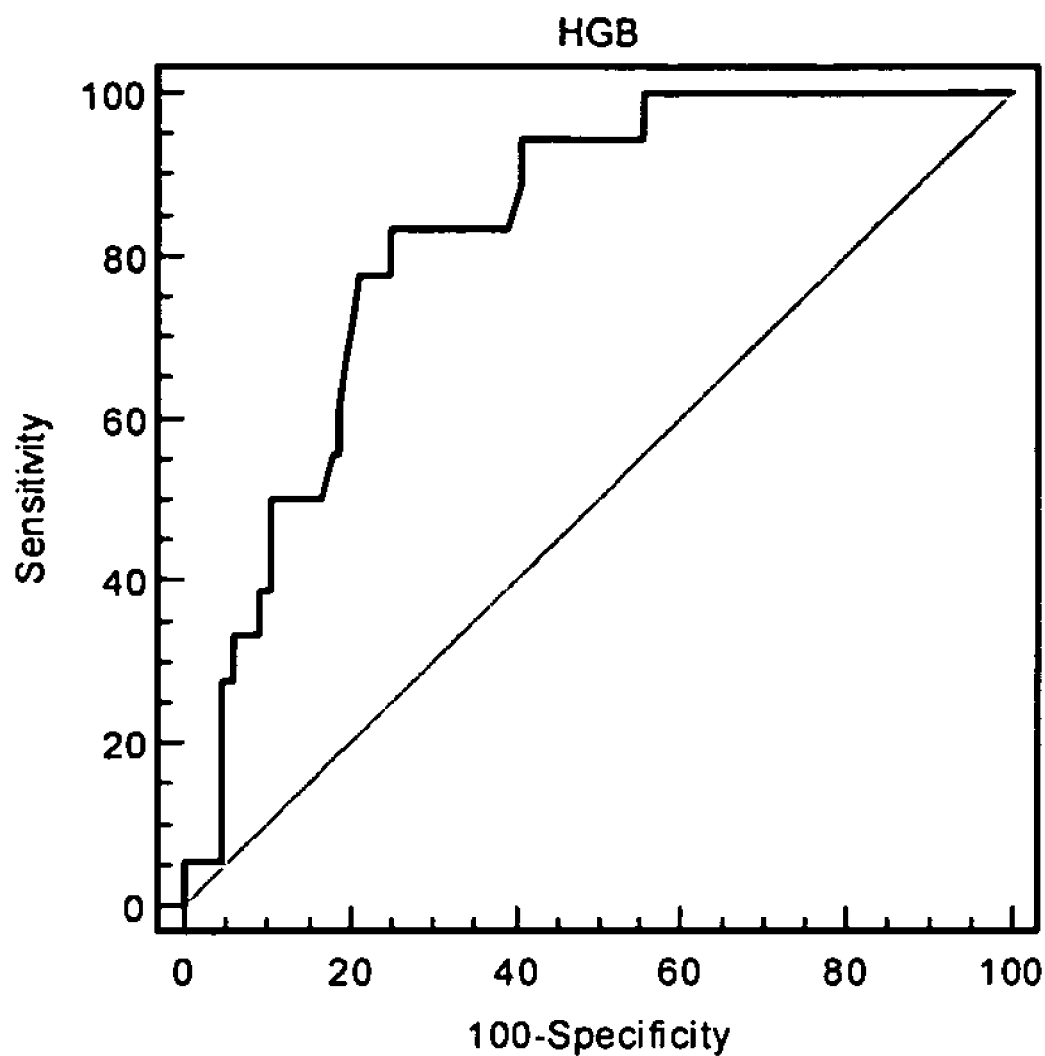
FIG. 4 is the ROC curve of Hgb for patients having TSAT between 20% and 30%.

In an exemplary embodiment, the predetermined criteria for defining the responder are TSAT between 20% and 30% and Hgb less than 10.0 (g/dl). As shown in the Example, for the patients who have TSAT between 20% and 30%, Hgb is effective for differentiating the responder and non-responder groups. FIG. 4 shows the ROC curve for Hgb. With a cut-off <9.98 (g/dl), the sensitivity and specificity of the method were 83.3% and 77.5%, respectively.

It can be appreciated that the method of the present invention using the new parameters RSf, VHf, VHDWf, RSHf and Hgb for determining the responsiveness of a patient to the r-HuEPO/i.v. iron treatment is a low cost approach. As described above, these parameters can be obtained from the automated reticulocyte measurement without additional cost. The turn-around time is very short, since one can obtain the hematology analysis results about 15 minutes after the blood collection from the patient. Furthermore, for determining the treatment protocol, RSf, CRP, serum ferritin and TSAT, together with the renal profile can be obtained in less than 3 hours, which can avoid multiple visits of a patient to the hospital.

In a further aspect, the present invention provides the method of using the above described new parameters for determining the r-HuEPO/i.v. iron treatment protocol. In one exemplary embodiment, the present invention provides a method of using RSf, TSAT and Hgb for determining the r-HuEPO/i.v. iron treatment protocol.

TABLE 1

Suggested Treatment Protocol Using TSAT, $RSf_1$ and Hgb

| | |
|---|---|
| $RSf_1$ <105.1, and TSAT <20% | Give r-HuEPO at full dose; Consider giving full dose of i.v. iron |
| TSAT >20% and <30% | If Hgb <10.0 g/dl, give r-HuEPO and i.v. iron at intermediate doses |
| $RSf_1$ >105.1, or TSAT >30% | Reduce iron doses. Consider other causes of anemia |
| CRP >50 and/or SF >500 ng/ml | Stop i.v. iron, regardless the values of TSAT and RSf. Treat inflammation/infection if possible, or consider increasing r-HuEPO/i.v. according the level of inflammation to unblock the iron. |

As illustrated in Table 1, if the patient has $RSf_1$ <105.1 and TSAT <20%, full doses of r-HuEPO and i.v. iron can be considered for the patient. If the patient has TSAT between 20% and 30%, and Hgb <10.0 g/dl, intermediate doses of r-HuEPO and i.v. iron can be considered. However, if the patient has $RSf_1$ >105.1, or TSAT >30%, the i.v. iron doses should be reduced, and other causes of anemia, such as folic acid deficiency, $B_{12}$ vitamin deficiency, aluminum intoxication, high CRP, etc., should be considered. In the situation when CRP >50 and/or serum ferritin >500 ng/ml, the r-HuEPO/i.v. iron treatment should be stopped, regardless the values of TSAT and $RSf_1$. Two approaches can be considered in this situation. In one approach, the patient is treated for inflammation/infection before giving further r-HuEPO/i.v. iron treatment. The second approach is based on the most recent realization that r-HuEPO is not only a red cell growth factor, but also a cytokine that counteracts the actions of the inflammatory proteins. In this approach, the markers for inflammation and the markers relating to the blockage in iron metabolism, such as hepcidin, interferon γ, and IL-6, are utilized for further identifying inflammation and iron blockage. If these are confirmed, the dosage of r-HuEPO at three times higher than its regular dosage can be used without iron for unblocking iron supply and as an anti-inflammatory treatment. It is noted that the second approach is used in the absence of inflammation caused by infection, which has to be treated with antibiotics.

The following examples are illustrative of the invention and are in no way to be interpreted as limiting the scope of the invention, as defined in the claims. It will be understood that various other ingredients and proportions may be employed, in accordance with the proceeding disclosure.

EXAMPLE 59 patients with renal failure in a treatment program of hemodialysis on alternate days were involved in the study. EPO/intravenous iron supplementation treatment (r-HuEPO/i.v. iron) was included in the program for associated anemia. Patients were followed up for a period of 5 months, and during this time 323 whole blood samples were collected at a regular interval of about one month at three hospitals, Academical Hospital of Maastricht (Holland), Marseille (France) and Bern (Switzerland).

The blood samples were analyzed on the Coulter GEN*S hematology analyzers (Beckman Coulter, Inc., Fullerton, Calif.), using the CBC and Retic modes. The hematology analyzers were operated under the standard operating condition. A first aliquot of 1.6 µl of a blood sample was diluted with Isoton 3E with a dilution ratio of 6250:1 to form a first sample mixture, which was measured by the DC impedance measurements to produce the red blood cell parameters. A second aliquot of 28 µl of the blood sample was diluted with 6 ml of Isoton 3E, and then mixed with 1 ml of Lyse S III diff to form a second sample mixture. The absorption of the second sample mixture was measured at about 540 nm to obtain Hgb. A third aliquot of 34 µl of the blood sample was mixed with 0.2 ml of Retic Stain, and then mixed with 2.0 ml of Retic Lyse to form the third sample mixture, which was measured by the VCS detection method to obtain the reticulocyte parameters. All reagents described above were the products of Beckman Coulter, Inc. The red blood cell parameters and reticulocyte parameters reported from the instrument were used for monitoring the patients for their response to the r-HuEPO/i.v. iron treatment.

Moreover, serum ferritin (SF) and transferrin were measured on an immunofluorometric assay on an AutoDelphia immunochemistry analyzer (Perkin-Elmer, Turku, Finland) and on an Array nephelometer (Beckman Coulter, Inc., Fullerton, Calif.), respectively. Transferrin saturation (TSAT) was calculated as the iron/transferrin molar ratio, divided by 2 (correction for two iron binding sites per transferrin molecule).

Iron supplementation during this period was decided based on the guidelines from the Dutch Kidney Foundation (Table 2). The guidelines recommend to give 200 mg iron when the TSAT is lower than 20% and SF is lower than 500 ng/ml; and to give 100 mg iron when the TSAT is lower than 20% and SF is between 500 and 800 ng/ml. Iron supplementation is withheld in any case when SF is higher than 800 ng/ml.

Since the average within-subject biological variation for Hgb is 4.42%, as defined in the literature (Fraser CG. The application of theoretical goals based on biological variation data in proficiency testing. *Arch Pathol Lab Med*. 1988 April; 112(4):404-15.), no less than 10% increase in Hgb in the next blood analysis (with a typical interval of about one month) was used as the criterion for defining the responder in this study.

TABLE 2

Iron Dosage Schedule (mg/month) According to the Guidelines of the Dutch Kidney Foundation

| | SF (µg/l) | | | |
|---|---|---|---|---|
| | <100 | 100-500 | 500-800 | >800 |
| TSAT <20% | 400 | 400 | 100 | none |
| TSAT >20% | 400 | 100 | none | none |

From the data analysis of 323 samples from these 59 patients, it was found that for all samples with a TSAT <20% and SF between 100 ng/ml and 500 ng/ml, there was a response to the r-HuEPO/i.v. iron treatment, with an increase of Hgb no less than 10% in the next blood analysis.

The red blood cell parameters and reticulocyte parameters reported from the hematology analyzers were compared between the responders and non-responders. It was found that MCV, MRV, MSCV, and Hgb had statistically significant differences between the responders and the non-responders, as shown in Table 3. It is noted that some of the samples had no reticulocyte parameters, which were not used for the analysis. Various functions of these parameters were also analyzed. The product functions of MCV, MRV and Hgb defined above were found to have statistically significant differences between the responders and non-responders and good sensitivity and specificity for clinical use. More specifically, these were $RSf_1$ as defined by $(MCV \times MRV)^{1/2}$ ($p<0.0001$); $RSf_2$ as defined by $(MCV \times MRV)/100$ ($p<0.0001$); VHf as defined by $(MCV \times Hgb)/100$ ($p<0.0001$);

and (MCV×MRV×Hgb)/1000 (p<0.0001). Herein, MCV and MRV were expressed in femtoliter (fl) and Hgb was expressed in gram per deciliter (g/dl).

The statistical functions of Microsoft® Excel 2000, the software programs MedCalc® Version 4.20.014 from Frank Schoonjans, and Method Validator (C) by Philippe Marquis, Metz, France were used for the statistical analysis.

Receiver operating characteristic (ROC) analyses were performed for these factors. It was found that for patients having TSAT <20%, the RBC size factor, both $RSf_1$ and $RSf_2$, volume-Hgb factor (VHf), and RBC size-hemoglobin factor (RSHf) were effective in differentiating the responders and non-responders.

Furthermore, it was found that for the patients who had TSAT between 20% and 30%, Hgb was a parameter effective for differentiating the responders and non-responders. FIG. 4 shows the ROC curve for Hgb. With a cut-off <9.98 (g/dl), the sensitivity and specificity were 83.3% and 77.5%, respectively.

The invention has been described with reference to particularly preferred embodiments. It will be appreciated, however, that various changes can be made without departing from the spirit of the invention, and such changes are intended to fall within the scope of the appended claims. While the present invention has been described in detail and pictorially shown in the accompanying drawings, these should not be construed

TABLE 3

Responders vs. Non-responders

| Patients with TSAT <20% | MCV | Hgb * MCV/100 | MRV | MSCV | MSCV/MCV |
|---|---|---|---|---|---|
| Non-responders n = 127 | 93.9 | 10.48 | 125.12 | 99.01 | 1.055 |
| Responders n = 12 | 88.23 | 8.42 | 112.91 | 93.23 | 1.057 |
| T-Student test | P < 0.0001 | P < 0.0001 | P = 0.0001 | P = 0.0012 | P = 0.8806 |
| ROC Curve Cut-off Proposed | ≦94.8 | ≦9.9 | ≦124.5 | ≦95.75 | |

| | $(MRV * MCV)^{1/2}$ | MRV * MCV/100 | MRV * MCV * Hgb/1000 | MRV/MCV | dR |
|---|---|---|---|---|---|
| Non-responders | 108.31 | 117.64 | 94.83 | 1.34 | 28.52 |
| Responders | 99.73 | 99.64 | 131.62 | 1.28 | 24.47 |
| T-Student test | P < 0.0001 | P < 0.0001 | P < 0.0001 | P = 0.0927 | P = 0.0795 |
| ROC Curve Cut-off Proposed | ≦105.1 | ≦110.47 | ≦111.50 | ≦1.27 | ≦25.8 |

FIGS. 1A and 1B show the ROC curves of $RSf_1$ and $RSf_2$, respectively, for patients having TSAT <20%. From the ROC analysis of $RSf_1$, the AUC was 0.881. With a cut-off ≦105.1, $RSf_1$ had a sensitivity of 100% and a specificity of 70.1%, respectively, for differentiating the responders and non-responders. From the ROC analysis of $RSf_2$, the AUC was 0.881. With a cut-off ≦110.5, $RSf_2$ also had a sensitivity of 100.0% and a specificity of 70.1%, respectively.

FIG. 2A shows the ROC curve of VHf for patients having TSAT <20%. From the ROC analysis of VHf, the AUC was 0.889. With a cut-off ≦9.9, VHf had a sensitivity of 91.7% and a specificity of 68.5%, respectively, for differentiating the responders and non-responders.

It was further found that VHf was also effective in differentiating the responders and non-responders for patients whose TSAT is higher than 20%. In this study, 150 blood samples had TSAT >20%. Among these, there were 18 responders and 132 non-responders, respectively, using the criterion defined above. FIG. 2B shows the ROC curve of VHf for patients having TSAT >20%. The AUC from the ROC analysis of VHf for this group of patients was 0.789. With a cut-off ≦10.5, VHf had a sensitivity of 77.8% and a specificity of 74.2%, respectively, for differentiating the responders and non-responders.

FIG. 3A shows the ROC curve of RSHf for patients having TSAT <20%. The AUC for RSHf was 0.927. With a cut-off ≦111.5, RSHf had a sensitivity of 100% and a specificity of 81.9%, respectively. FIG. 3B further shows the ROC curve of RSHf for patients having TSAT >20%. For this group of patients, the AUC for RSHf was 0.766. With a cut-off >122.5, RSHf had a sensitivity of 66.7% and a specificity of 78.0%, respectively.

as limitations on the scope of the present invention, but rather as an exemplification of preferred embodiments thereof. It will be apparent, however, that various modifications and changes can be made within the spirit and the scope of this invention as described in the above specification and defined in the appended claims and their legal equivalents. All patents and other publications cited herein are expressly incorporated by reference.

What is claimed is:

1. A method of determining responsiveness of a patient to recombinant human erythropoietin therapy comprising the steps of:
    (a) analyzing a blood sample of said patient on a hematology analyzer and obtaining a mean cell volume of red blood cells (MCV) and a total hemoglobin concentration (Hgb) of said blood sample;
    (b) obtaining a volume-hemoglobin factor (VHf) of said blood sample, defined as a product function of said MCV and said Hgb;
    (c) comparing said VHf obtained in step (b) to a predetermined VHf criterion that defines a responder to said recombinant human erythropoietin therapy; and
    (d) reporting an indication of said responder if obtained VHf meets said predetermined VHf criterion.

2. The method of claim 1, wherein said VHf is defined by the formula of (MCV×Hgb)/100.

3. The method of claim 2 further comprising analyzing a further blood sample of said patient on a clinical chemistry analyzer, and obtaining transferrin saturation (TSAT) of said further blood sample.

4. The method of claim 2, wherein said predetermined VHf criterion of said responder is ≦9.9 when said patient has a transferrin saturation (TSAT) less than 20%, and wherein said MCV is measured in femtoliter and said Hgb is in gram/deciliter.

5. The method of claim 2, wherein said predetermined VHf criterion of said responder is ≦10.5 when said patient has a transferrin saturation (TSAT) higher than 20%, and wherein said MCV is measured in femtoliter and said Hgb is in gram/deciliter.

6. The method of claim 1 further comprising obtaining red blood cell distribution width (RDW) from said analysis in step (a); obtaining a volume-hemoglobin/red blood cell distribution width factor (VHDWf) of said blood sample, defined as a function of said MCV said Hgb and said RDW; comparing said VHDWf to a predetermined VHDWf criterion that further defines said responder to said recombinant human erythropoietin therapy; and reporting an indication of said responder if said VHDWf meets said predetermined VHDWf criterion.

7. The method of claim 6, wherein said VHDWf is defined by the formula of (MCV×Hgb)/(RDW×10).

8. The method of claim 1 further comprising using said TSAT in combination with VHf in determining responsiveness of said patient.

9. The method of claim 1 further comprising using said TSAT to determine a treatment protocol.

10. The method of claim 1 further comprising obtaining a mean cell volume of reticulocytes (MRV) from said analysis in step (a); obtaining a RBC size-hemoglobin factor (RSHf) of said blood sample, defined as a product function of said MCV, said MRV and said Hgb; comparing said RSHf to a predetermined RSHf criterion that further defines said responder to said recombinant human erythropoietin therapy; and reporting an indication of said responder if said RSHf meets said predetermined RSHf criterion.

11. The method of claim 10, wherein said RSHf is defined by the formula of (MCV×MRV×Hgb)/1000.

12. The method of claim 11 further comprising using said TSAT in combination with RSHf in determining responsiveness of said patient.

13. The method of claim 11 further comprising using said TSAT to determine a treatment protocol.

\* \* \* \* \*